United States Patent [19]

Brook

[11] Patent Number: 4,902,565
[45] Date of Patent: Feb. 20, 1990

[54] WATER ABSORBENT STRUCTURES

[75] Inventor: Michael G. Brook, Chessington, England

[73] Assignee: Fulmer Yarsley Limited, Surrey, England

[21] Appl. No.: 225,204

[22] Filed: Jul. 28, 1988

[30] Foreign Application Priority Data

Jul. 29, 1987 [GB] United Kingdom ................ 8717949

[51] Int. Cl.$^4$ ........................... B32B 3/26; B32B 7/12
[52] U.S. Cl. .................................. 428/315.5; 428/284;
428/315.9; 428/316.6; 428/317.1; 428/913;
604/368; 604/369
[58] Field of Search ................. 428/284, 315.5, 315.9,
428/316.6, 317.1, 913; 604/368, 369

[56] References Cited

U.S. PATENT DOCUMENTS 4,826,723  5/1989  Brambach ......................... 428/284

*Primary Examiner*—William J. Van Balen
*Attorney, Agent, or Firm*—Burns, Doane, Swecker & Mathis

[57] ABSTRACT

Water absorbent structures are disclosed which are intended for use as wound dressings, disposable nappies (diapers) or similar applications. The structures comprise a flexible porous substrate, e.g. an open-cell foam web which is impregnated with (a) a solid, water-insoluble water absorber which has a fine particle size and is capable of absorbing at least 30 times its weight of water and (b) a hydrophilic binder which retains the water absorber in the substrate and comprises a substantially non-cross-linked, water-insoluble, hydrogel forming polymer.

Component (a) has a high affinity for water due to the presence of hydrophilic groups in the polymer, but is insoluble in water and in common organic solvents. Component (b) is also water-insoluble, but because of its non-cross-linked structure is soluble in common organic solvents, such as ethanol.

9 Claims, 2 Drawing Sheets

WATER ABSORBENT STRUCTURES

This invention relates to water-absorbent structures and to a method for their preparation. Structures which are capable of absorbing several times their own weight of water or aqueous fluids, such as body fluids, are useful in the preparation of articles such as would dressings, disposable nappies, sanitary towels, materials for filling urostomy bags and for analagous purposes.

Hydrophilic cross-linked polymers have been developed which are capable of absorbing up to about five times their own weight of water to yield elastic hydrogels. Such materials have found widespread use in contact lens manufacture and in biological and surgical inplants. Other kinds of hydrophilic polymers are known, which in their non-hydrated, finely-divided state, are capable of about 100 times their own weight or more. Their use in water-absorbent structures of the kind indicated above is, however, restricted by difficulties of retaining the water-absorbent polymers in relation with some suitable substrate. Typically, such highly water-absorbing materials are insoluble in most solvents and cannot be cast, or formed, by thermoforming procedures.

European Patent Application No. 0 041 934 (Ferrosan) describes a foamed plastic structure for application to wounds in which the foamed plastic is impregnated with a particulate, hydrophilic, water-swellable polymer and a water-soluble binder. Because the binder is water-soluble, is it leached out of the foamed plastics structure by exudate from the wound. Recognising this problem, the inventors of the above European application select water-swellable polymers of a specific particle size which is small enough to enter the pores of the foam but are intended to swell to such a size in use that the swollen particles become trapped in the pores of the foam and do not escape from the foamed plastics structure.

Wound dressings are however subject to mechanical stretching and flexing in use and the effective trapping of swollen particles of polymer in the foam is not considered to be a safe or reliable method of retaining the particles within the dressing. Since such swollen particles will contain absorbed wound exudate, the escape of such particles from the dressing is highly undesirable since it could give rise to cross-infection.

SUMMARY OF THE INVENTION

According to one aspect of the resent invention there is provided a water-absorbent structure which is capable of absorbing and retaining at least several times its dry weight of water aqueous liquids and which comprises:

(a) a flexible, porous substrate which is substantially unaffected by water and which is impregnated with:

(b) a solid, water-insoluble, water-absorbing material which is capable of absorbing at least 30 times its dry weight of water, and (c) a hydrophilic binder retaining the water-absorbing material in the substrate, said binder comprising a substantially non-cross-linked, water-insoluble, hydrogel-forming polymer.

SOLID WATER-ABSORBING MATERIAL

The water-absorbing solid materials are particulate (preferably finely-powdered), cross-linked hydrophilic polymers, which are insoluble in water and in most organic solvents. However, the polymers contain a high concentration of hydrophilic groups which gives them high water absorbing and retaining properties. Examples of suitable polymer materials are acrylic polymers containing amide, acid (e.g. carboxylic acid), or alkali metal salt groups. For example, the hydrophilic polymers may be polymers or copolymers of acrylamide or polymers of one or more acrylic monomers with acrylic or methacrylic acid. When unsaturated acid monomers are employed, the acid groups may be neutralised by treatment with an alkali metal hydroxide, such as sodium hydroxide. The unsaturated acid or amide monomers are copolymerised with a minor proportion of cross-linking agent, (e.g. from about 0.1 to 5% by weight of the monomers), using a di- or poly-functional unsaturated cross-linking agent, e.g. a glycol diacrylate, divinyl benzene, a triallyl compound or N,N-methylene-bis-acrylamide. Preferably, the particulate, water-absorbing material has a particle size of less than 50 microns ($\mu$m). One commercially available material is sold by Allied Colloids Ltd. under the trade name ALCOSORB AB3F. This is a finely-divided acrylamide polymer which is cross-linked with methylene bis acrylamide. Alcosorb can hold up to 400 times its own weight of water. However, its water-holding capacity is reduced in the presence of metal cations, especially di and poly-valent cations. Another commercially available material which may be employed as the water absorbing material is sold under the trade name Salsorb 84, also by Allied Colloids Ltd. Salsorb 84 is a cross-linked polymer of acrylic acid and slats thereof, e.g. sodium salts.

It may also be possible to use as the water-absorbing material a lightly cross-linked polymer of N-vinyl pyrrolidone.

Whatever the chemical nature of the water-absorbing material, it should have a hydration capacity of at least about 30 and generally of at least 50. Hydration capacity is defined for the purpose of the present application, as the ratio of the mass of the water-swollen material to that of the dry material and is determined by the following test:

A ½ grm sample of the material is weighed into a 100 ml centrifuge tube, 50 ml of distilled water of pH 6.4 are added and the tube shaken vigorously until a suspension is formed. The tube is shaken again after 5 and 10 minute intervals. The tube is centrifuged for 15 minutes with a rotational frequency of 2000 min$^{-1}$, the supernatant liquid is decanted off and the tube and its contents are then reweighted.

For the intended uses of the structure of the present invention, the liquid which is absorbed will generally be an aqueous liquid (e.g. a body fluid) containing dissolved salts. Thus, in the resulting water-absorbing structure the water-absorbing solid material will in general have an actual hydration capacity in use which is less than that indicated by the above test. However, for the purposes of selecting suitable materials, it is convenient to measure the property of materials by the above test.

POROUS SUBSTRATE

The porous substrate may be any material which is sufficiently flexible for the purposes of the particular use, is unaffected by water and provides a large surface area. Ideally, it should be wetted by the solution used to impregnate the substrate with the water-absorbing material and the hydrogel-forming polymer, but not be soluble in the solution. In the construction of nappies and sanitary towels, the substrate would normally be a cellulose material, such as wood pulp fibre, but may be of other porous materials, such as elastomeric foam or glass or synthetic fibrous material.

In the case of would dressings, the porous substrate is preferably a foamed plastics material having interconnecting cells. The foam need not be hydrophilic and polyurethane/polyether foams are preferred. Foams having a fine pore size are advantageous, as the greatest surface area and fastest water uptake is thereby obtained. Open cell polyurethane polyether foams having a density of 15 to 100 kg per cubic metre may be employed as the porous substrate. Preferred foams have a density of 20 to 50 kg per cubic metre. Where the water-absorbing structure is to be used as a wound dressing, a microporous backing membrane is preferably applied to one surface of the foam in order to prevent the wound drying out too quickly or leakage of exudate from the wound and consequent risk of cross infection. A backing membrane will also prevent ingress of dirt, infection or other undesirable fluids. Suitable microporous backing membranes include polyurethanes, polyvinyl chloride, or polypropylene. Such materials can be manufactured by calendaring a web of the polymer containing a dispersed water-soluble salt and then washing out the salt. Typical manufacturing processes are described in U.K. Pat. No. 1,099,676. Commercially available microporous membranes include Porvair. Such materials may be in the form of thin films having a thickness of about 50 to 150 $\mu$m (micrometres). Alternatively, thicker layers may be used for their strength and cushioning properties which typically have a thickness of about 700 to 800 $\mu$m (micrometres). In either case the membrane may be adhesively bonded to one surface of the plastics foam to form a laminate. The bonding step is advantageously carried out prior to impregnating the foam with the water-absorbing material. Heat activatable adhesives are generally the most satisfactory and suitable techniques include printing the adhesive onto the membrane, followed by bonding to the foam, or simultaneously bonding the adhesive, in the form of a heat activatable adhesive interlayer, to the foam and the backing membrane.

The selection of solid, water absorbing materials having a fine particle size enables a uniform distribution of the water absorbing material through the foam, or other porous structure, to be obtained, even where there is a low loading of hydrophilic binder and water absorbing material.

THE HYDROPHILIC BINDER

The third component of the water-absorbent structure is the hydrogel-forming binder and this should be a substantially non-cross-linked hydrophilic polymer so that this it is soluble in some organic solvents, but insoluble in water. Preferably, the hydrophilic binder is of the kind described in our co-pending British patent application No. 87 11357 (Publication No. 2,190,387), and the corresponding U.S. application Ser. No. 050019, filed May 15, 1987. Such polymers are essentially uncross-linked copolymers of hydrophobic monomer components and hydrophilic polymer components, wherein the hydrophobic monomer component is selected from at least one ester of an unsaturated acid of the general formula $CH_2=CRCOOR^1$, where R is hydrogen or $CH_3$ and $R^1$ is a linear or branched chain alkyl group and wherein the hydrophilic monomer component is selected from one or more of N-vinyl pyrrolidone, acrylic or methacrylic acid and esters of acrylic and methacrylic acid of the general formula $CH_2=CRCOOR^2$, where R is hydrogen or methyl and $R^2$ is an hydroxy terminated alkyl or alkoxy group. Preferably, the hydrophilic monomer consists of or comprises N-vinyl pyrrolidone and the hydrophobic monomer is a lower alkyl ester of acrylic or methacrylic acid, e.g. methyl methacrylate.

The hydrophilic nature of the binder depends inter alia on the particular hydrophobic and hydrophilic comonomers and the proportions in which they are copolymerised. An increase in the molar proportions of the hydrophilic component will result in a copolymer having a higher capacity for water absorption and accordingly a resultant hydrogel having a higher water content. In general, the aim is to produce a copolymer which is capable of absorbing at least 180%, preferably at least 200%, of its weight of water.

A further desirable, but not essential, component of the water-absorbent structure is a hydrophilic plasticiser. Suitable plasticisers may be selected from polyalkylene glycols, e.g. polypropylene glycol and polyethylene glycol with a molecular weight of about 500 to 1500. The presence of the hydrophilic plasticiser prevents embrittlement of the water-absorbent structure in the dry state.

Water-absorbent structures in accordance with the invention may be prepared by dispersing the water-absorbing polymer material in a solution of the hydrophilic binder and the plasticiser in a suitable solvent, such as ethanol or methylated spirit. After impregnating the substrate with the dispersion, it is dried to remove the solvent. The aim is to introduce an amount of water-absorber mixture (i.e. solid water absorbing material plus hydrophilic binder), of at least 15 grams per 100 grams of porous substrate and usually between about 20 to 40 grams per 100 grams, based on the dry weight.

The water-absorbent structure can be incorporated in the manufacture of a nappy or like article, as the absorbent core of a structure which includes a water-impervious backing sheet and a porous hydrophobic top sheet, through which the urine may flow into the core to be retained. Methods of manufacture of disposable nappies are described, for example, in U.S. Pat. Nos: 3,592,194, 3,489,148 and 3,860,003.

Alternatively, the water-absorbing structure may be designed for use as a wound dressing. In this case, the porous substrate is generally a foam web but may be impregnated with the same kind of dispersion of the water-absorbing material.

BRIEF DESCRIPTION OF THE DRAWINGS

In the accompanying drawings,

FIG. 1 shows schematically one method of bonding the foam to the membrane. A microporous web is drawn from spool 1, a foam web from spool 2 and a hot melt interlayer e.g. an ethylene vinyl acetate (hereinafter eva) interlayer from spool 3. The three webs are brought together at a nip formed by a pair of rollers 4 & 5, one of which is a metal roller heated to a temperature which will actuate the eva adhesive (e.g. about 80° C.) and the other is rubber. A roller diameter of about 150 mms for the metal roller is a suitable size. The ethylene vinyl acetate interlayer film is a reticulated or discontinuous film.

The foam layer of the resulting laminated structure may be impregnated with a dispersion of the water-absorbing material in an organic solvent solution of the hydrophilic binder. Although a web of the unlaminated foam can be impregnated with the water-absorbing composition by squeezing the foam prior to entry into a bath of the composition and releasing the compressed foam under the liquid, other techniques are desirable in the case of laminated foams, in order to prevent the hydrophilic binder sealing the pores in the microporous backing web. FIG. 2 shows schematically a suitable apparatus. The laminated web 21 is drawn upwardly from a spool (not shown) between a pair of rollers 22 and 23 and a wedge of water-absorbing composition 24 is maintained between the foam side 25 of the laminate and the roller 23. Upstream of the impregnating station a second nip is provided by rollers 26 and 27 to remove excess impregnating composition and the laminate is then guided around roller 29 into a drying chamber 28 from which it is taken up on a spool 20. The direction of rotation of the rollers is indicated by arrows. Web 21 is drawn upwardly through the apparatus by rotation of spool 30. Compression is applied to the web by rollers 22 and 23 which causes impregnation of the foam.

FIG. 3 shows a disposable nappy which comprises a backing sheet 30 which is water-impervious. Located on the backing sheet 30 is an appropriately shaped porous core 31 which may be of open-cell foam material but is preferably foamed from wood pulp fibre. The core 31 is impregnated with a water absorbing mixture as described above. A covering layer (shown partially broken away) comprising a water-permeable sheet 32 is applied over the core 30 and overlaps onto edges 33 of the backing sheet. An adhesive may be coated onto the edges 33 of the backing sheet in order to retain the core and form an integral structure. Draw tapes or other attachment means may be secured to the backing sheet.

FIG. 4 shows a section through a wound dressing in accordance with the invention which comprises a backing membrane 41 formed from a microporous air-permeable but water-impermeable material. Bonded to the backing membrane is a web of foamed polymer material 42 having a fine-pored, open cellular structure. The laminate formed from membrane 41 and foam web 42 may be impregnated with a water-absorbent dispersion using the technique described above in connection with FIG. 2. Foam web 42 is bonded to membrane 41 using a hot melt adhesive, e.g. by the method described above in connection with FIG. 1. A pressure sensitive adhesive 43 may be applied to the edges of the backing membrane 41 to facilitate attachment of the wound dressing to a patient's skin.

Figure 1:
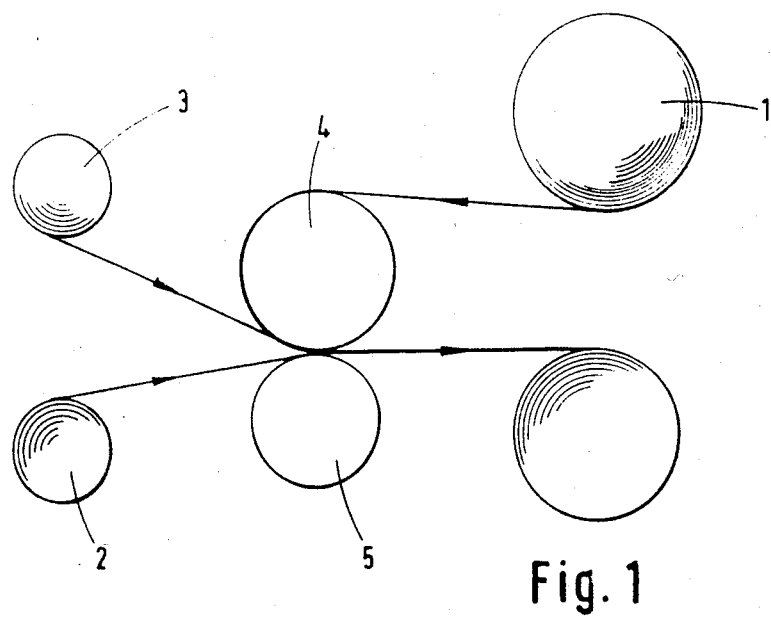
FIG. 1 shows schematically one method of bonding a web of foam to a backing membrane.

The foam web 42 should be several times thicker than the membrane 41. Since one clinical use of the wound dressings is for treatment of pressure sores (decubitus ulcers), the foam is preferably sufficiently thick to provide some cushioning effect by reducing high contact pressures between the patient's skin and a bed. Suitable thicknesses for the foam are from about 1 to 15 mm, preferably 5 to 10 mm.

The following Examples, in which parts are by weight, illustrates the preparation of water-absorbent structure in accordance with the invention.

EXAMPLE 1

A non-cross-linked hydrophilic binder was prepared by copolymerising methyl methacrylate and vinyl-pyrrolidone in accordance with Example 9 of our co-pending British patent application No. 87 11357 (Publication No. 2,190,398). 16 parts of the resulting solid copolymer were dissolved in methylated spirits together with 20 parts of polypropylene glycol having a molecular weight of 1025. 64 parts of a finely-divided solid cross-linked polyacrylamide sold by Allied Colloids Limited under the trade name Alcosorb AB 3F was dispersed in the resulting solution. A strip of polyether foam was impregnated with the resulting dispersion and oven-dried to evaporate the solvent. On testing, it was found that the dried impregnated polyether foam (having a calculated surface area of 60 sq cm and containing 0.4 grms of the impregnating material comprising the cross-linked polyacrylamide, the hydrogel-forming binder and the plasticisers) absorbed 14.5 grms of a test solution of "artificial urine". The artificial urine had the formulation set out below. This was equivalent to a hydration capacity based on the solid impregnating material of 36. The artificial urine was retained and was not lost by manipulation of the foam. Scaling the procedure up and taking a standard disposable nappy having an absorbent core with a surface area of about 800 sq.cms. and impregnating the core with about 5 grms of water-absorbing polymer, plasticiser and hydrophilic binder, a nappy can be produced which would have a urine absorbing capacity of about 1090 grms.

| Artificial Urine Formulation ARTIFICIAL URINE | |
|---|---|
| Urea | 25 g/l |
| Sodium chloride | 6 |
| Potassium chloride | 3 |
| Sodium carbonate | 2 |
| Ammonium hydroxide | 1 |
| Calcium chloride | 1 |
| Hydrochloric acid to pH | 6-7 |
| From Biochemistry, Lehninger, Pub. by Worth Publishers, p. 840. | |

EXAMPLE 2

Figure 2:
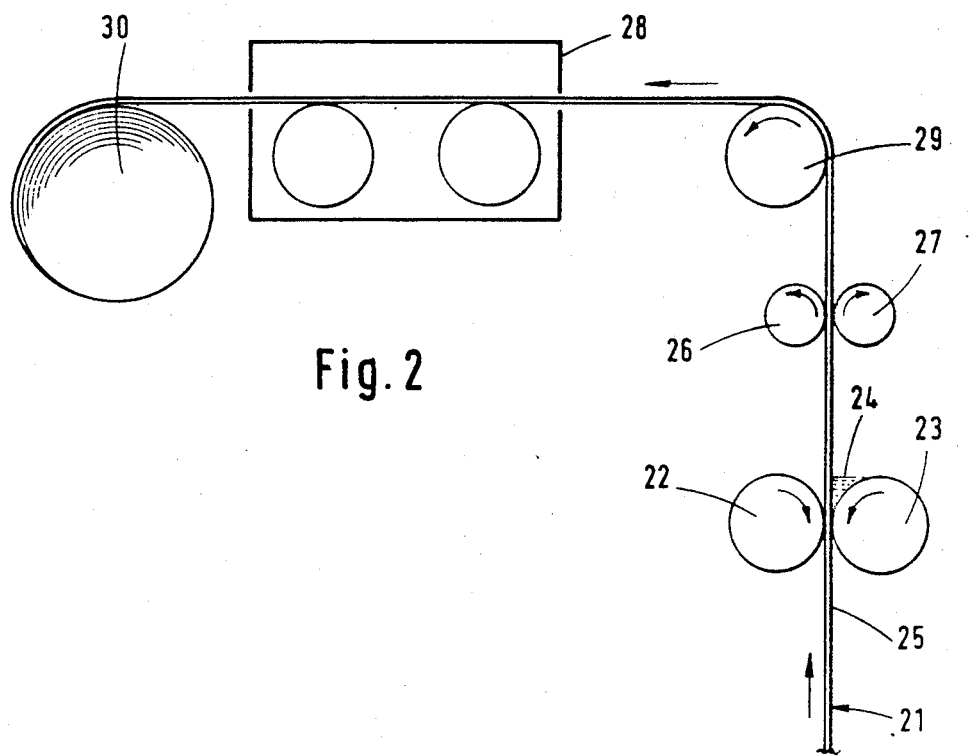
FIG. 2 shows schematically a method of impregnating a foam web with a dispersion of water-absorbing solid material in a solution of the hydrophilic binder.
Figure 3:
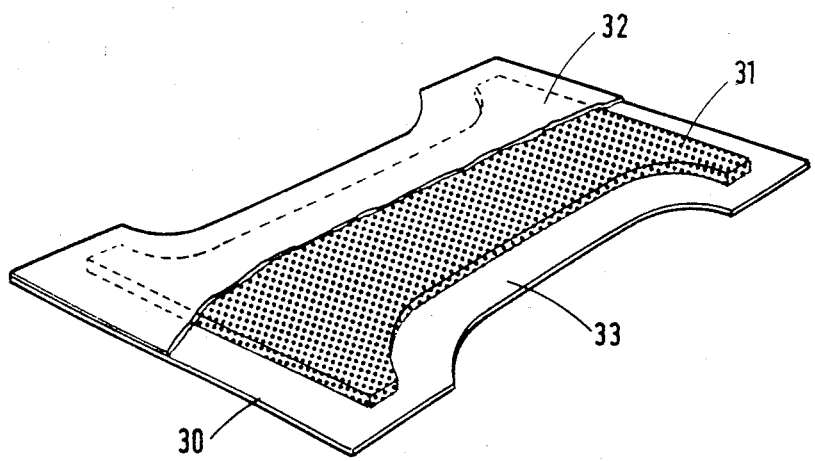
FIG. 3 is a perspective view of a disposable nappy (diaper) constructed in accordance with the invention.
Figure 4:
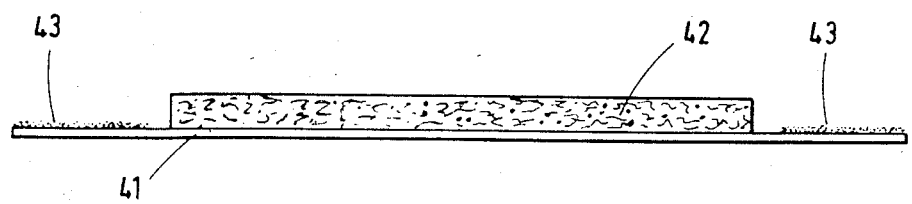
FIG. 4 is a sectional view of a wound dressing in accordance with the invention.

The same hydrophilic binder used in Example 1 was dissolved in methylated spirit to form a solution containing 16 parts of the solid copolymer, together with 10 parts of polypropylene glycol of molecular weight 1025, per 60 parts of solvent. 86 parts of a finely divided water-absorbent material sold by Allied Colloids Ltd. under the trade name Salsorb 84 (a cross-linked polymer of acrylic acid in which acid groups were neutralised with sodium ions) were dispersed in 100 parts of the binder solution. The resulting dispersion was impregnated with the foam web of a laminate of a foam web and a microporous polyurethane membrane, using the technique described above in connection with FIG. 2. A discontinuous eva interlayer was used to bond the foam web to the microporous membrane. The foam web was about 7 mm thick and was an open-cell polyurethane polyether having a density of 29 kg/cubic metre.

After drying, the resulting laminate had a loading of absorbent mixture (i.e. the Salsorb, polypropylene glycol and the hydrophilic binder) of 40 parts per 120 parts of foam.

I claim:

1. A water-absorbent structure which is capable of absorbing and retaining, at least, several times its dry weight of water aqueous liquids and which comprises:
   (a) a flexible, porous substrate which is substantially unaffected by water and which is impregnated with:
   (b) a solid, water-insoluble, water-absorbing material which is capable of absorbing at least 30 times its dry weight of water, and
   (c) a hydrophilic binder retaining the water-absorbing material in the substrate, said binder comprising a substantially non-cross-linked, water-insoluble, hydrogel-forming polymer.

2. A structure according to claim 1 in which the hydrogel-forming polymer is an essentially non-cross-linked copolymer of hydrophobic monomer components and hydrophilic monomer components, wherein the hydrophobic monomer component is selected from at least one ester of an unsaturated acid of the general formula $CH_2=CRCOOR^1$, where R is hydrogen or $CH_3$ and $R^1$ is a linear or branched chain alkyl group and wherein the hydrophilic monomer component is selected from one or more of N-vinyl pyrrolidone, acrylic or methacrylic acid and esters of acrylic and methacrylic acid of the general formula $CH_2=CRCOOR^2$, where R is hydrogen or methyl and $R^2$ is an hydroxy terminated alkyl or alkoxy group.

3. A structure according to claim 1 in which the flexible porous substrate in bonded on one side to a microporous membrane.

4. A structure according to claim 2 in which the microporous membrane is a polyurethane, p.v.c. or polypropylene polymer and the flexible porous substrate is a plastics foam having interconnecting cells.

5. A structure according to claim 4 in which the plastics foam is bonded to the microporous membrane with a heat activatable adhesive.

6. A structure according to claim 1, in which the solid, water-absorbing material is a cross-linked acrylic or methacrylic polymer containing pendant amide, acid or salt groups.

7. A structure according to claim 6 in which the water-absorbing material is a cross-linked polymer of acrylamide.

8. A structure according to claim 1, which additionally contains a watermiscible plasticiser.

9. A structure according to claim 8 in which the plasticiser to a polyalkylene glycol.

* * * * *